(12) United States Patent
Luquire

(10) Patent No.: US 6,578,578 B2
(45) Date of Patent: Jun. 17, 2003

(54) EYE MASKS TO FACILITATE SLEEPING UNDER CERTAIN CONDITIONS

(75) Inventor: L. Hanson Luquire, Montomery, AL (US)

(73) Assignee: Abstrac Products, Inc., Montgomery, AL (US)

( * ) Notice: Subject to any disclaimer, the term of this patent is extended or adjusted under 35 U.S.C. 154(b) by 0 days.

(21) Appl. No.: 09/543,815

(22) Filed: Apr. 6, 2000

(65) Prior Publication Data

US 2002/0174871 A1 Nov. 28, 2002

(51) Int. Cl.[7] ................................................. A61F 11/00
(52) U.S. Cl. ...................................... 128/857; 128/858
(58) Field of Search ............................... 128/846, 847, 128/858; 2/7, 8, 9, 10

(56) References Cited

U.S. PATENT DOCUMENTS

| 2,005,426 A | 6/1935 | Land |
| D159,344 S | 7/1950 | Jonaitis |
| 2,813,459 A | 11/1957 | Archambault |
| 2,844,994 A | 7/1958 | Filler |
| 3,901,589 A | 8/1975 | Bienenfeld |
| 3,967,885 A | 7/1976 | Byler |
| 4,012,129 A | 3/1977 | Byler |
| 4,057,852 A | 11/1977 | Contant |
| 4,113,364 A | 9/1978 | Dussich |
| 4,149,780 A | 4/1979 | Young |
| 4,229,082 A | 10/1980 | Carreau et al. |
| 4,271,538 A | * 6/1981 | Mortesi ........................ 2/439 |
| 4,279,474 A | 7/1981 | Belgorod |
| 4,396,259 A | 8/1983 | Miller |
| 4,411,263 A | 10/1983 | Cook |
| D281,329 S | 11/1985 | Harrell |
| D291,447 S | 8/1987 | Fletcher et al. |
| D294,952 S | 3/1988 | Wilson |
| 4,790,031 A | * 12/1988 | Duerer ........................ 128/858 |
| 4,877,320 A | 10/1989 | Holden |
| 4,908,878 A | 3/1990 | Tarragano |
| 4,952,043 A | 8/1990 | Werner et al. |
| 4,976,530 A | 12/1990 | Mackay et al. |
| 4,977,029 A | 12/1990 | Brown et al. |
| 5,005,214 A | 4/1991 | Koethe |
| 5,259,830 A | 11/1993 | Masuda |
| 5,390,369 A | 2/1995 | Tubin |
| 5,435,006 A | 7/1995 | Kitayama |
| 5,546,141 A | 8/1996 | Wheatley |
| 5,552,841 A | 9/1996 | Gallorini et al. |
| 5,614,963 A | 3/1997 | Parker |
| D388,812 S | 1/1998 | Miehe et al. |
| 5,867,247 A | * 2/1999 | Martin ........................ 351/177 |
| D410,021 S | 5/1999 | Heyman et al. |
| 5,956,760 A | * 9/1999 | Wine ................................ 2/9 |
| 6,056,400 A | * 5/2000 | Knepp ........................ 351/155 |
| 6,145,983 A | * 11/2000 | Schiffer ........................ 351/46 |

* cited by examiner

Primary Examiner—Michael A. Brown
(74) Attorney, Agent, or Firm—Dean W. Russell; Camilla C. Williams; Kilpatrick Stockton LLP

(57) ABSTRACT

Eye masks having nose- and ear-pieces similar to those of conventional spectacles and sunglasses are described. Such masks include eye-covering regions of opaque material but need not include elastic bands, adhesive, or loops to retain the regions in place while in use. The masks additionally may be made of one-piece construction if desired, molded of plastic or other suitable material into a unitary body.

6 Claims, 5 Drawing Sheets

EYE MASKS TO FACILITATE SLEEPING UNDER CERTAIN CONDITIONS

FIELD OF THE INVENTION

This invention relates to masks for eyes and more particularly to opaque eye shields similar to spectacles or sunglasses but designed to facilitate sleeping under conditions (as in airplanes, trains, and cars, for example) where the wearer's environment may be illuminated.

BACKGROUND OF THE INVENTION

The disclosure of U.S. Pat. No. Des. 388,812 to Miehe, et al. appears exemplary of conventional styles of sleeping masks. Such masks typically include a fabric or cloth body to which one or more elastic bands are attached. In use, the body is positioned over the eyes of the wearer and generally held in place when the elastic bands are stretched about the wearer's head. Additionally, because the body is wholly flexible, it conforms, more or less, to the contours of the face of the wearer in the region it covers.

Omission of a relatively rigid nose- or ear-piece of the mask of the Miehe patent, however, can result in slippage of the body of the mask in use. This slippage in turn may decrease the comfort of the wearer, potentially waking him or her from restful sleep. These flexible masks further lack any stylishness, resembling neither aesthetically-attractive spectacles nor sunglasses.

U.S. Pat. No. 4,411,263 to Cook describes infant eye shields designed as alternatives to the traditional practice of taping gauze pads over infants' eyes during hospital procedures. As with other conventional masks, the eye shields of the Cook patent are made of flexible cloth (or film) and omit any rigid nose- or ear-piece. Instead, the shields are adhered to the temples of infants using adhesive of selected peel and shear strengths, with such adhesive being utilized to maintain the shields in position.

U.S. Pat. No. 4,908,878 to Tarragano, incorporated herein in its entirety by this reference, details yet another light shield, although for use primarily (but supposedly not exclusively) with hospitalized adults. It too "is made entirely of soft, non-woven fabric sheeting," intentionally omitting any more rigid plastic or other material. Loops attached to the masking region of the shield engage the ears of a wearer to retain the shield in place. Although the Tarragano patent mentions (without explanation) "ultrasonically welding" the periphery of the shield and its loops, it nevertheless fails to suggest having any rigid masking region or nose- or ear-piece or structure resembling conventional spectacles or sunglasses.

SUMMARY OF THE INVENTION

The present invention, by contrast, provides more rigid masks or shields intended to block all (or substantially all) visible light from the eyes of the wearer. Such masks do not include elastic bands, adhesive, or loops to maintain them in position in use. Rather, relatively rigid nose- and ear-pieces are employed, in some respects similar to those of existing spectacles and sunglasses.

Additionally unlike conventional shields, the eye-covering regions of the innovative masks likewise are relatively rigid in comparison with cloths or fabrics. Thus, masks of the present invention may be made of one-piece construction, molded of plastic or other suitable material into a unitary body. If desired, frames of the masks may have some flexibility, much as many spectacle frames currently do, to permit at least some adjustment for enhanced conformance to features of the wearers' heads.

It thus is an object of the present invention to provide eye masks lacking any need for elastic bands, adhesive, and loops to permit their retention in position.

It is also an object of the present invention to provide eye masks whose frames and contours can be similar to those of attractive or stylish spectacles or sunglasses.

It is another object of the present invention to provide eye masks having opaque material in place of lenses so as to block some or all visible light from penetrating the masks to the wearers' eyes.

It is a further object of the present invention to provide eye masks having nose-pieces, ear-pieces, or both made of material other than flexible cloth or fabric.

It is an additional object of the present invention to provide eye masks which may be molded of plastic material and which may be of one-piece construction.

It is yet another object of the present invention to provide eye masks which facilitate sleeping in places, such as in cars, airplanes, and trains or outdoors, where ambient light may be present.

Other objects, features, and advantages of the present invention will be apparent to those skilled in the art with reference to the remaining text and drawings of this application.

DETAILED DESCRIPTION

Figure 1:
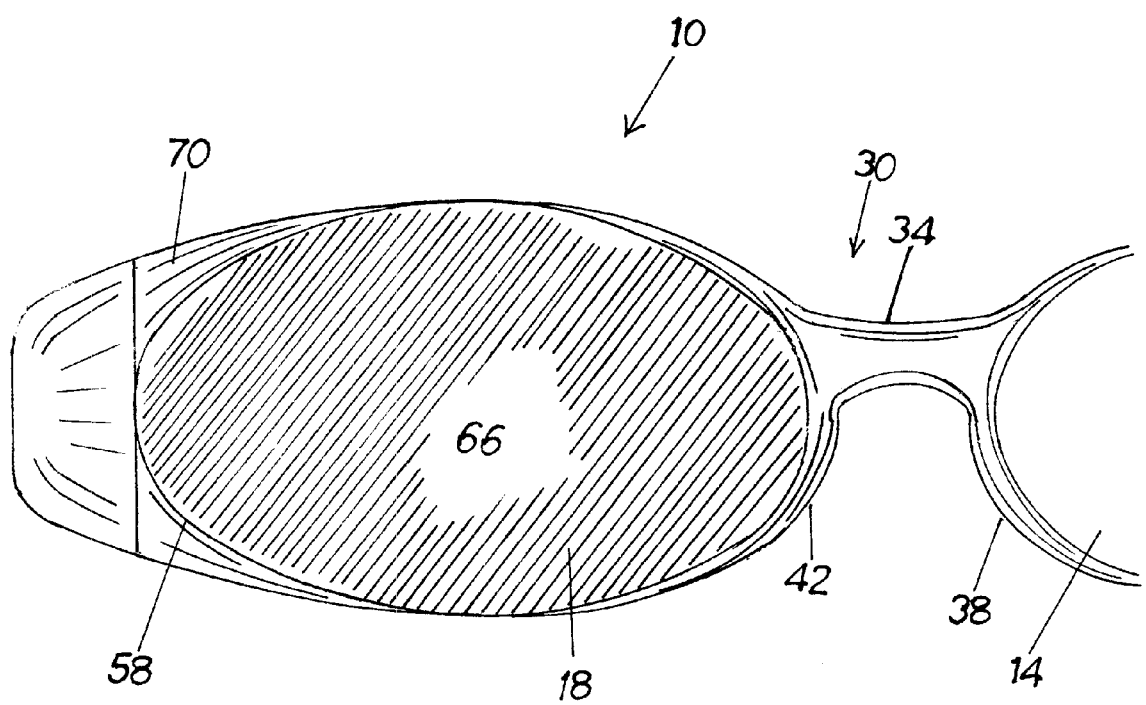
FIG. 1 is a front elevational view of portions of an eye mask of the present invention.

FIGS. 1–4 illustrate an exemplary eye mask 10 of the present invention. Mask 10 typically includes eye-covering regions 14 and 18, associated respectively with the left and right eyes of a wearer. Also incorporated into mask 10 are ear-pieces 22 and 26 and nose-piece 30, the latter of which comprises either or both of bridge 34 and pads 38 and 42. Ear-piece 22 is adapted to contact the left ear of a wearer, while ear-piece 26 contacts the wearer's right ear. Nose-piece 30, by contrast, contacts the wearer's nose in use, with bridge 34 also functioning to connect regions 14 and 18.

Preferred embodiments of mask 10 are molded of plastic material having sufficient rigidity to maintain its overall shape absent application of manual or other pressure. Some embodiments of mask 10 presently contemplated will not change shape during any portion of normal use. Other embodiments, however, may permit a wearer to flex or bend (at least slightly) either or both of ear-pieces 22 and 26 and bridge 34 to adapt mask 10 better to the characteristics of the wearer's head. In either event, by making regions 14 and 18, ear-pieces 22 and 26, and nose-piece 30 of the same material, mask 10 can be of one-piece construction whether molded or otherwise formed.

At least regions 14 and 18 should be opaque for optimal results. Creating these regions 14 and 18 of black material of sufficient thickness to prevent all (or substantially all) visible light from reaching the wearer's eyes is preferred in connection with mask 10, although those skilled in the art are aware that materials or colors other than black may be utilized instead. Thus, although some embodiments of mask 10 may be solid black in color, others may be or contain other colors (and indeed may be multi-colored if appropriate or desired).

If ear-pieces 22 and 26 are formed of substantially rigid material and mask 10 is of one-piece construction, ear-pieces 22 and 26 will not fold compactly like corresponding ear-pieces of conventional glasses. These versions of mask 10 are contemplated as being sufficiently inexpensive so as to be disposable after use rather than requiring storage. Of course, regardless of cost they need not necessarily be disposed of following use, and other embodiments of mask 10 may include hinges or other suitable mechanisms allowing ear-pieces 22 and 26 to fold more or less parallel to the general plane containing regions 14 and 18.

As noted earlier, ear-pieces 22 and 26 are designed to contact the wearer's ears when mask 10 is being used. The ear-pieces 22 and 26 of FIGS. 2–4 likely will contact only the upper portions of the wearer's ears, in the uppermost areas of connection of the ears to the head. As shown particularly in FIG. 4, such ear-pieces 22 and 26 are relatively straight. Ear-pieces 22 and 26 need not be so formed, however, but instead may include terminal hooks (in essence, they may be shaped so as to resemble a rotated letter "J") to engage additional portions of the wearer's ears.

Figure 2:
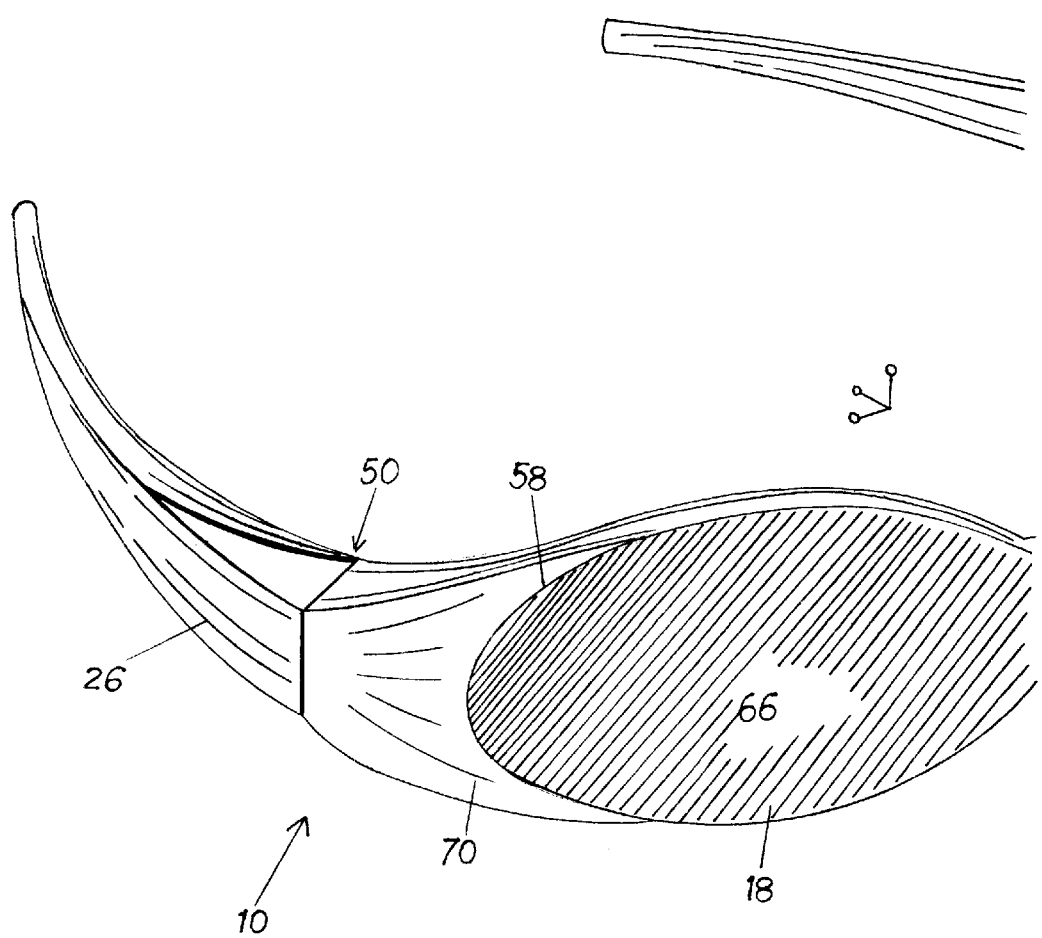
FIG. 2 is a perspective view of portions of the eye mask of FIG. 1.
Figure 3:
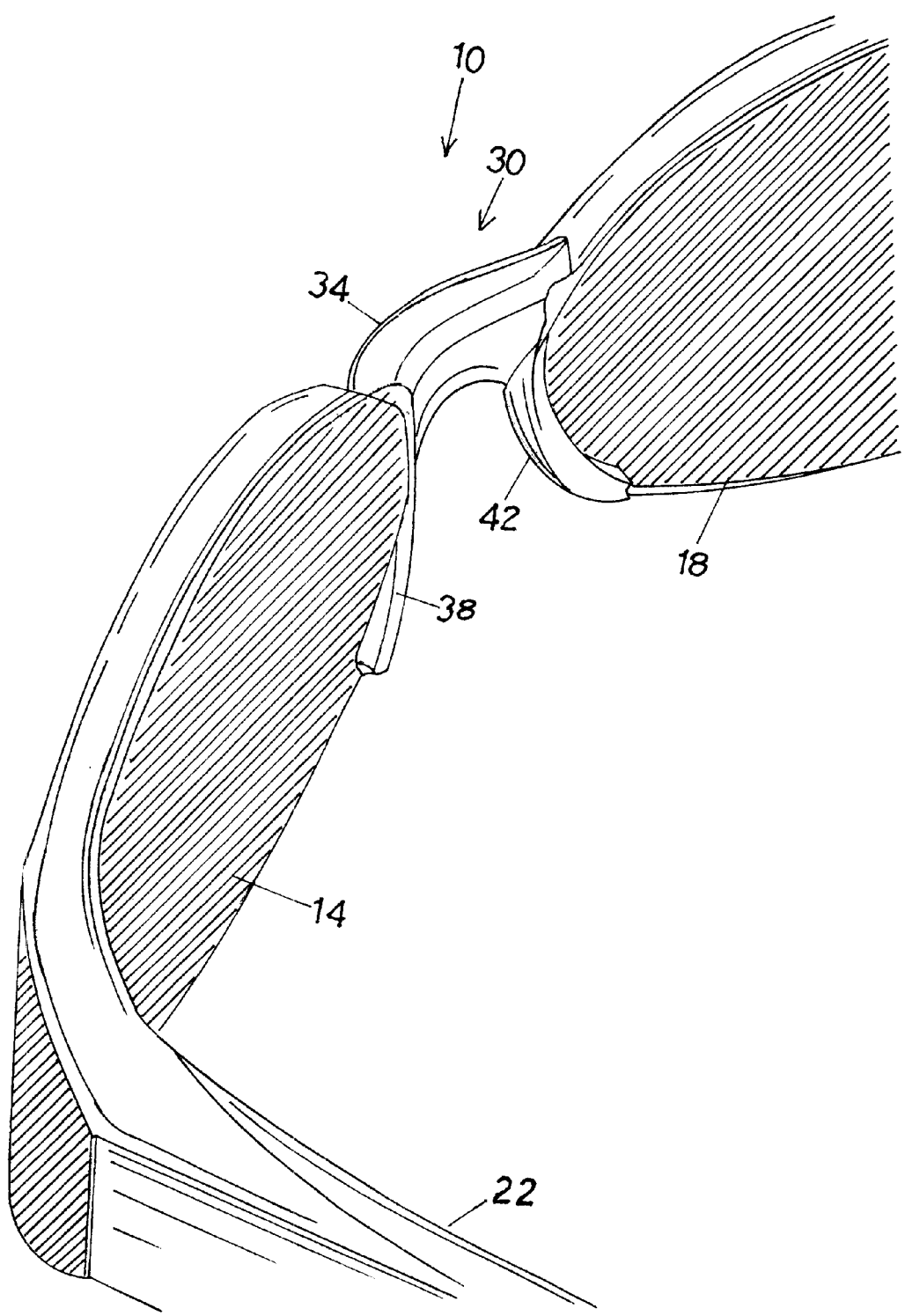
FIG. 3 is another perspective view of portions of the eye mask of FIG. 1.
Figure 4:
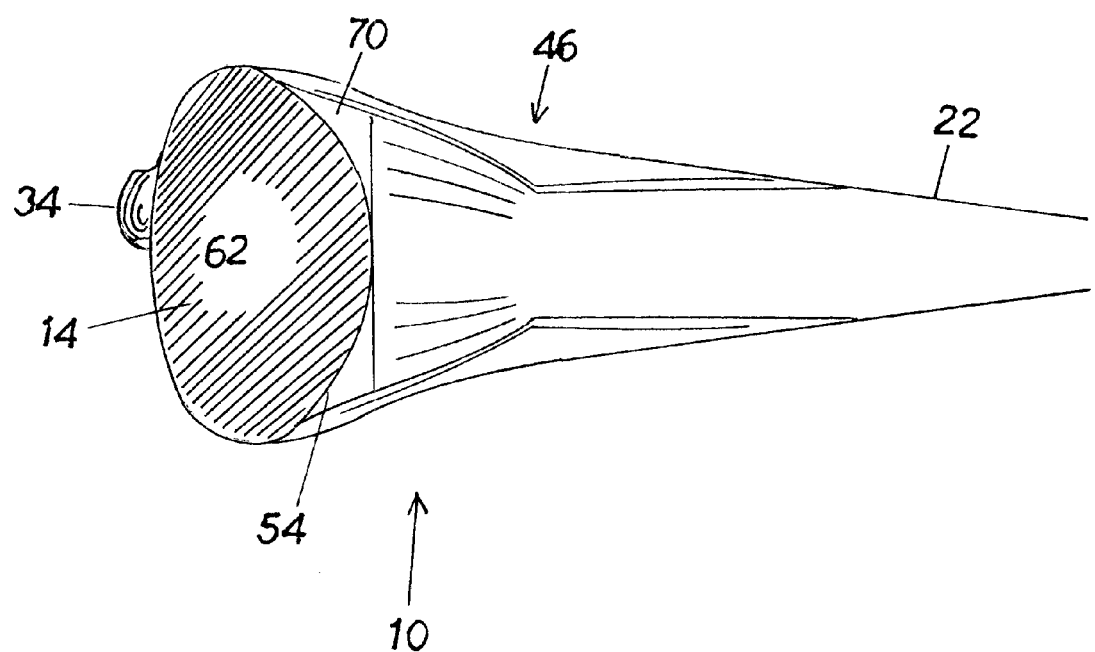
FIG. 4 is a side view of portions of the eye mask of FIG. 1.

Additionally as shown in FIGS. 2 and 4, each of ear-pieces 22 and 26 may include a portion 46 or 50 of increased width near the junction of pieces 22 and 26 with regions 14 and 18. Increased-width portions 46 and 50 may be useful in inhibiting visible light from reaching the eyes peripherally and thus, if present, advantageously may be made of opaque material. Portions 46 and 50 need not have width greater than the remainder of ear-pieces 22 and 26, however.

Together with ear-pieces 22 and 26, nose-piece 30 helps maintain the position of mask 10 on a wearer's head. Typically either not bendable or only modestly so, bridge 34 of nose-piece 30 is adapted to contact and rest against the bridge of the wearer's nose. Pads 38 and 42, in turn, contact and rest against opposed sides of the wearer's nose. If in the form shown in FIG. 3, pads 38 and 42 may comprise curved, increased-thickness areas of respective regions 14 and 18. Pads 38 and 42 may be formed otherwise, however, if appropriate.

FIGS. 1, 2, and 4 collectively illustrate ridges 54 and 58, which may demarcate respective central sections 62 and 66 of regions 14 and 18 from frame 70. If, hypothetically, lenses were substituted for central sections 62 and 66, ridges 54 and 58 effectively could indicate or overlap the edges of the lenses adjacent the frame of the glasses. Thus, in embodiments of mask 10 where ridges 54 and 58 (or either of them) are present, the ridges 54 and 58 can simulate (at least aesthetically) the presence of lenses and thereby enable the mask 10 more to resemble spectacles or sunglasses.

Figure 5:
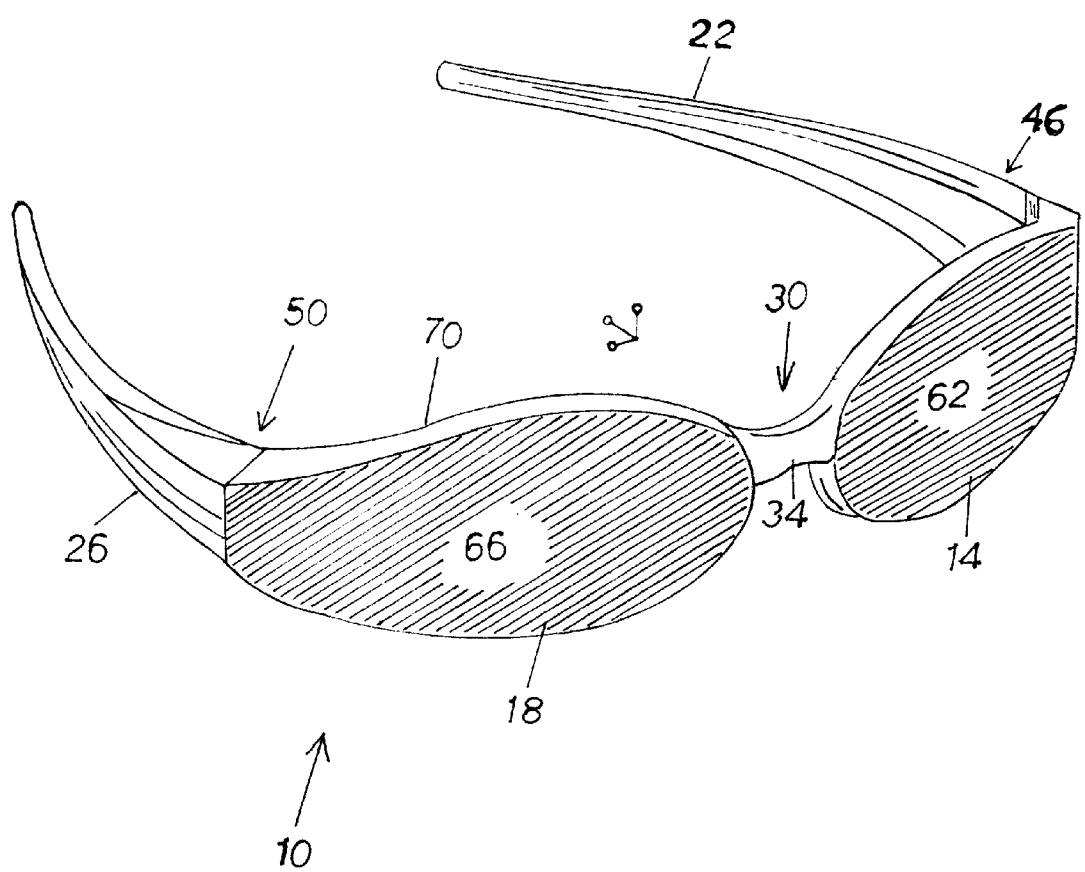
FIG. 5 is a perspective view of an alternate eye mask of the present invention.

FIG. 5, by contrast, details an alternative mask 10' lacking any ridges 54 or 58 or demarcations between central sections 62 and 66 and the remainder of frame 70 in regions 14 and 18. Frame 70 thus may be smooth throughout regions 14 and 18, unlike conventional spectacles and sunglasses. This characteristic of mask 10' may simplify its being molded, for example, while additionally creating a sleeker, potentially more attractive appearance for the mask 10'.

The foregoing is provided for purposes of illustrating, explaining, and describing embodiments of the present invention. Further modifications and adaptations to these embodiments will be apparent to those skilled in the art and may be made without departing from the scope or spirit of the invention.

I claim:

1. A mask comprising:
    a. a frame defining first and second regions of substantially rigid, opaque molded material which, in use, is fitted over the entire forward viewing areas of respective left and right eyes of a human being so as to preclude the human being seeing through the frame; and
    b. first and second substantially rigid, molded ear-pieces connected to the frame and adapted to be positioned in contact with the respective left and right ears of the human being.

2. A mask according to claim 1 further comprising a substantially rigid, molded nose-piece connecting portions of the frame and adapted to be positioned in contact with the nose of the human being.

3. A mask according to claim 2 in which the first region of opaque material and the nose-piece are molded simultaneously.

4. A mask according to claim 1 omitting any elastic bands, adhesives, or loops and in which the first ear-piece includes a portion of increased width adjacent the first region of opaque material.

5. A mask according to claim 1 further comprising a ridge demarcating the boundary between the frame and first region of opaque material.

6. A mask according to claim 1 omitting any demarcation between the frame and first region of opaque material so that the interface between the frame and first region of opaque material is smooth and continuous.

* * * * *